United States Patent [19]
Häsler et al.

[11] Patent Number: 5,824,698
[45] Date of Patent: Oct. 20, 1998

[54] ANTIBACTERIAL DIBENZIMIDAZOLE DERIVATIVES

[75] Inventors: Walter Häsler; Yu-Hua Ji, both of Basel; Werner Leupin, Liestal, all of Switzerland

[73] Assignee: Hoffman-La Roche Inc., Nutley, N.J.

[21] Appl. No.: 836,423

[22] PCT Filed: Nov. 2, 1995

[86] PCT No.: PCT/CH95/00255

§ 371 Date: May 14, 1997

§ 102(e) Date: May 14, 1997

[87] PCT Pub. No.: WO96/16042

PCT Pub. Date: May 30, 1996

[30] Foreign Application Priority Data

Nov. 17, 1994 [CH] Switzerland .............................. 3459/94

[51] Int. Cl.$^6$ ........................ A61K 31/415; C07D 235/18
[52] U.S. Cl. .......................................... 514/394; 548/305.4
[58] Field of Search .......................... 548/310.7, 304.7, 548/306.1, 305.4; 514/394

[56] References Cited

U.S. PATENT DOCUMENTS

| | | | |
|---|---|---|---|
| 3,592,821 | 7/1971 | Schellenbaum et al. | 548/310.7 |
| 4,087,409 | 5/1978 | Preston | 528/229 |
| 4,665,066 | 5/1987 | Morin, Jr. | 514/206 |
| 4,960,790 | 10/1990 | Stella et al. | 514/449 |
| 5,412,059 | 5/1995 | Connelle et al. | 528/183 |

OTHER PUBLICATIONS

Preston, Chemical Abstracts, vol. 71, abstract 125249d, 1969.
Niume et al., Chemical Abstracts, vol. 96, abstract 143422g, 1982.
Haga et al., Jounal of the Chemical Society, Dalton Transactions, pp. 263–271, 1994.
*The Chemistry of Heterocyclic Compounds*, Part 1, 40:1–285 (1981) (not enclosed).
Coville, N. and E. Neuse, *J. Org. Chem.*, 42:3485–3491 (1977).
Hein, D.W., et al., *J. Amer. Chem. Soc.*, 79:427–429 (1957).
Phillips, M.A., *J. Chem. Soc.*, pp. 2393–2399 (1928).
Potts, K.T., *Comprehensive Heterocyclic Chemistry*, 5:457–487 (1984).
Preston, P.N., *Chemical Review*, 74:279–314 (1974).
Yadagiri, B., and J.W. Lown, *Synth. Commun.*, 20:955–963 (1990).
Smith, Jr., J.G. et al. *Polymer Preprints*, vol. 32, pp. 193–194 (1991).
Kapodia, A.B. et al. *J. Macromol. Sci.—Chem.*, vol. A18, pp. 831–838 (1982).
Brand, R.A. et al. *J. Polymer Science: Polymer Chemistry Edition*, vol. 17, pp. 1145–1152 (1979).
Haga, M. et al. *Inorg. Chem.*, vol. 30, pp. 3843–3849 (1991).

*Primary Examiner*—Richard L. Raymond
*Attorney, Agent, or Firm*—George W. Johnston; Dennis P. Tramaloni; Alan P. Kass

[57] ABSTRACT

Novel and known dibenzimidazoles of the formula $$R^1 - \underset{\underset{H}{N}}{\overset{N}{\bigg\langle}} \!\!\! \underset{}{\bigcirc}\!\!\!-\!\!\!\underset{}{\bigcirc} \!\!\! \underset{\underset{H}{N}}{\overset{N}{\bigg\rangle}} - R^2 \qquad \mathrm{I}$$

wherein

R$^1$ and R$^2$ can be the same or different and signify $C_6H_4R^3-$, $C_6H_3(OH)R^4-$ or heterocyclyl, R$^3$ signifies hydroxy, amino, lower alkoxy or cyano and R$^4$ signifies halogen, lower alkyl or lower alkoxy, as well as pharmaceutically usable salts of compounds of general formula I are antibacterials, especially against Staphylococcus, Enterococcus and *Heliobacter pylori*.

12 Claims, No Drawings

ANTIBACTERIAL DIBENZIMIDAZOLE DERIVATIVES

CROSS REFERENCE TO RELATED APPLICATION

This application is an application under 35 U.S.C. § 371 of International Application No. PCT/CH95/00255 which designated the United States.

The invention is concerned with dibenzimidazole derivatives. In particular, it is concerned with 2,2'-bis-substituted 6,6'-dibenzimidazoles of the general formula

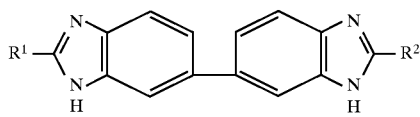

wherein
$R^1$ and $R^2$ can be the same or different and signify $C_6H_4R^3$—, $C_6H_3(OH)R^4$— or heterocyclyl,
$R^3$ signifies hydroxy, amino, lower alkoxy or cyano and
$R^4$ signifies halogen, lower alkyl or lower alkoxy, as well as pharmaceutically usable salts of compounds of general formula I.

These compounds are novel with the exception of
4-[2'-(4-hydroxy-phenyl)-6,6'-dibenzimidazol-2-yl]-phenol,
3-[2'-(3-hydroxy-phenyl)-6,6'-dibenzimidazol-2-yl]-phenol,
4-[2'-(4-amino-phenyl)-6,6'-dibenzimidazol-2-yl]-phenylamine, and
4-[2'-(4-cyano-phenyl)-6,6'-dibenzimidazol-2-yl]-benzonitrile.

The compounds of formula I and their pharmaceutically usable salts exhibit a very good antibacterial activity, primarily against gram-positive pathogens such as Staphylococcus and *Enterococcus faecalis*. Further, they also exhibit a good activity against *Helicobacter pylori*.

They are therefore suitable for the prophylaxis and treatment of illnesses which are caused by such pathogens.

Symmetrical bis-benzimidazoles have been described in the literature as starting materials for the preparation of polybenzimidazoles (J. Org. Chem., 42, 3485–3491 [1977]). The use of these compounds as therapeutically active substances, especially for the prevention or treatment of bacterial diseases, is novel.

Objects of the present invention are compounds of general formula I and pharmaceutically usable salts thereof for use as therapeutically active substances, especially as active substances against bacterial pathogens; medicaments containing one or more compounds of general formula I defined in claim 1 or pharmaceutically usable salts thereof; the use of these compounds in the control or prevention of illnesses which are caused by bacterial pathogens and for the production of medicaments for the mentioned indications; as well as the novel compounds of formula II, their pharmaceutically usable salts as well as the manufacture of these novel compounds and salts.

The term "lower alkyl" used in the present description conveniently denotes those with up to 7, preferably up to 4, C atoms such as methyl, ethyl, n-propyl, isopropyl, n-butyl, isobutyl, s-butyl, t-butyl and the like.

Halogen signifies chlorine, bromine, fluorine or iodine.

The term "lower alkoxy" denotes a lower alkyl residue bonded via an oxygen atom.

In accordance with the present description the term "heterocyclyl" signifies a 5- or 6-membered unsaturated ring with at least one hetero atom such as O, S or N, for example furyl, pyranyl, thienyl, pyrrolyl or pyridyl.

Especially preferred for use as therapeutically active substances are those compounds of formula I in which $R^1$ and $R^2$ are the same or different and signify $C_6H_4R^3$— or $C_6H_3(OH)R^4$—, $R^3$ and $R^4$ have the significance given above and wherein a substituent preferably occupies a 4-position or optionally a 3-position on the phenyl ring.

It has been found that the antibacterial activity is especially high when the substituent $R^3$ or $R^4$ or the hydroxy group in $C_6H_3(OH)R^4$— for $R^1$ or $R^2$ is situated in the 4-position.

Thus, compounds in which a hydroxy group is situated in the 4-position on the phenyl ring are particularly preferred. The following compounds are particularly preferred for use as therapeutically active substances:

4-[2'-(4-Hydroxy-phenyl)-6,6'-dibenzimidazol-2-yl]-phenol;
3-[2'-(3-hydroxy-phenyl)-6,6'-dibenzimidazol-2-yl]-phenol;
4-[2'-(4-amino-phenyl)-6,6'-dibenzimidazol-2-yl]-phenylamine;
2-fluoro-4-[2'-(3-fluoro-4-hydroxy-phenyl)-6,6'-dibenzimidazol-2-yl]-phenol;
4-[2'-(4-hydroxy-3-methoxy-phenyl)-6,6'-dibenzimidazol-2-yl]-2-methoxy-phenol;
5-[2'-(3-hydroxy-4-methoxy-phenyl)-6,6'-dibenzimidazol-2-yl]-2-methoxy-phenol;
2,2'-bis-(4-methoxy-phenyl)-6,6'-dibenzimidazole;
2,2'-bis-(4-ethoxy-phenyl)-6,6'-dibenzimidazole;
4-[2'-(4-ethoxy-phenyl)-6,6'-dibenzimidazol-2-yl]-phenol;
4-[2'-(4-hydroxy-phenyl)-6,6'-dibenzimidazol-2-yl]-benzonitrile.

The symmetrically substituted compounds of formula I in which $R^1$ and $R^2$ have the same significance can be manufactured in accordance with the invention by reacting the compound of the formula

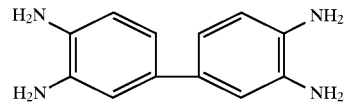

with an excess of a reactive compound which yields the residue $R^1$ or $R^2$.

The unsymmetrically substituted compounds of formula I in which $R^1$ and $R^2$ do not have the same significance can be manufactured in accordance with the invention by reacting the compound of formula II simultaneously with two different reactive compounds which yield the residues $R^1$ and $R^2$.

A further possibility for the manufacture of symmetrical or unsymmetrical compounds of formula I comprises reacting a compound of the formula

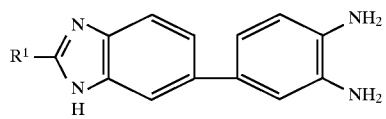

wherein $R^1$ has the above significance, with a reactive agent which yields the residue $R^1$ or $R^2$.

Not only the symmetrically substituted compounds, but also the unsymmetrically substituted compounds of formula I can, if desired, be converted into a pharmaceutically usable salt.

The following can be used, for example, as reactive compounds which are suitable for the manufacture of the compounds of formula I:

3- or 4-Hydroxy-benzaldehyde,
4-hydroxy-benzoic acid ethyl imide ester,
4-amino-benzaldehyde,
3-fluoro-4-hydroxy-benzaldehyde,
4-hydroxy-3-methyl-benzaldehyde,
4-hydroxy-3-methoxy-benzaldehyde,
4-methoxy-benzaldehyde,
4-ethoxy-benzaldehyde,
3-hydroxy-4-methoxy-benzaldehyde, furancarboxylic acid ethyl imide ester,
4-cyano-benzaldehyde.

Other appropriately substituted aldehydes, acids, esters, anhydrides, alkyl imides or acyl halides (described in Chem. Rev. 74, 279–314; The Chemistry of Heterocyclic Compounds, Part I, Vol. 40, pp. 1–286, 1981; Comprehensive Heterocyclic Chemistry, Vol. 5, pp. 457–487) are also suitable.

For the manufacture of the symmetrically substituted compounds of formula I, 3,3'-diamino-benzidine (II) is reacted with a reactive compound which yields the residue $R^1$ or $R^2$.

This is conveniently carried out by reacting the 3,3'-diamino-benzidine with a 2-fold amount of the reactive derivative in a solvent, e.g. ethanol, for several hours at the boiling temperature of the solvent which is used.

$Na_2S_2O_5$ or nitrobenzene is especially suitable as an additive for the manufacture of the compounds of formula I when aldehydes are used as the reactive derivatives. When acids, esters, anhydrides, alkyl imides or acyl halides are used, HCl (J. Chem. Soc., 2393–2399, [1928]), polyphosphoric acid (J. Amer. Chem. Soc. 79, 427–429 [1957]) or optionally nitrobenzene (Synth. Commun. 20, 955–963 [1990]) are suitable.

The manufacture of unsymmetrically substituted dibenzimidazoles can be effected in a similar manner.

Starting from 3,3'-diamino-benzidine (II) the reaction is effected with two different reactive compounds, for example with two different substituted aldehydes.

Thus, the compound 4-[2'-(4-ethoxy-phenyl)-6,6'-dibenzimidazol-2-yl]-phenol is obtained, for example, by reacting 3,3'-diamino-benzidine with 4-hydroxy-benzaldehyde and 4-ethoxy-benzaldehyde in ethanol and addition of $Na_2S_2O_5$ after stirring for several hours at reflux.

The reaction solution also contains the corresponding symmetrical compounds in addition to the unsymmetrically substituted dibenzimidazoles.

Symmetrically or unsymmetrically substituted dibenzimidazole derivatives are also obtained by reacting a compound of the formula

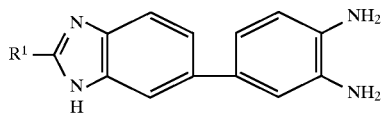

III with an aforementioned reactive compound which yields the residue $R^1$ or $R^2$. The reaction is effected analogously to the procedure described above.

The pharmaceutically usable salts can be manufactured according to known methods. For example, the free bases of formula I can be converted into the corresponding salts with the following inorganic or organic acids: hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like.

Preferred salts are the hydrochlorides which can be manufactured from the basic compounds of formula I, e.g. with a methanolic HCl solution.

The starting compounds required for the manufacture of the compounds of formula I are known commercially available products, e.g. compound II, or can be prepared readily according to methods known per se.

Thus, e.g. the compound III can be obtained by reacting 3-amino-3'-nitro-benzidine with a reactive compound which yields the residue $R^1$, for example with 4-hydroxy-benzaldehyde, with the nitro group of the isolated intermediate being subsequently hydrogenated to the amino group. The hydrogenation is effected according to procedures described in the literature, for example with hydrogen or hydrazine in the presence of Raney-nickel.

The compound III obtained can then, as described, be converted with a further compound which yields the residue $R^1$ or $R^2$ into the dibenzimidazoles of formula I. All reactive compounds which contain the residue $R^1$ or $R^2$ and which are required for the manufacture of the compound I are known compounds and/or can be prepared in an analogous manner according to procedures described in the literature.

For example, 4-hydroxybenzoic acid ethyl imide ester can be prepared as follows:

4-Hydroxy-benzonitrile in a solvent mixture, for example in a chloroform-ethanol mixture, is treated several times at room temperature with dry HCl gas, with the resulting hydrochloride being separated at intervals. The resulting ester can then be converted into compounds of formula I without further purification.

As mentioned earlier, the substituted 6,6'-dibenzimidazoles of formula I and their pharmaceutically usable salts have extremely valuable pharmacological properties. Table 1 shows their activity (in vitro) against various bacterial strains, primarily their very good activity against gram-positive bacteria.

Evaluation of the antibacterial activity

The minimum inhibitory concentration (MIC) of the substances investigated against gram-positive and gram-negative strains was determined using standard agar methods. The compounds were dissolved in a small amount of dimethyl sulphoxide, diluted with water and incorporated into liquified DST agar at 50° C. The thus-produced agar plates were used immediately thereafter in the test. The test concentrations lay between 128 and 0.06 µg/ml. The bacterial inoculation solutions were prepared from pre-cultures grown overnight, diluted and applied to the agar surface using an inoculation device (Denley A400). The plates were incubated at 35° C. for 20 hours. The MIC was determined as the lowest concentration of substance which prevented a visible growth. A scarcely visible turbidity and the growth of less than 5 colonies were ignored. The determinations of the antibacterial activities (Tab. 1) were carried out not only for the free bases, but also for the hydrochloride salt of each compound. The same values were obtained within experimental error.

The antibacterial activities against *Helicobacter pylori* were carried out analogously to the method described above with the following variations: The compounds were incorporated into Müller-Hinton agar containing 5% sheep blood additive. The test concentrations lay between 10 and 0.1 µg/ml. The pre-incubation time was 5 days, the incubation time was 4 days for *H. pylori* K 1585 and 7 days for *H. pylori* PN 81.

TABLE 1

Antibacterial activity in vitro
Minimum inhibitory concentration (MIC) in μg/ml

Structure: R¹–[benzimidazole]–[benzimidazole]–R²  (I)

| Bacterial strain | Example 5<br>R¹ = R² = –C₆H₄–OH (para) | Example 6<br>R¹ = R² = –C₆H₄–OH (meta) | Example 7<br>R¹ = R² = –C₆H₄–NH₂ (para) |
|---|---|---|---|
| E. coli 1346 | ≦0.12 | 2.00 | ≦0.12 |
| E. coli DC2 | ≦0.12 | 1.00 | ≦0.12 |
| E. coli 25922 | >128 | >128 | >128 |
| E. coli 1527 E | >128 | >128 | >128 |
| E. coli 159 R | >4 | | |
| E. coli B | ≦0.12 | 0.50 | 0.25 |
| E. coli K12 KEA-12 (GyrA) | >128 | >128 | >128 |
| E. coli H560 | >128 | >128 | >128 |
| E. coli AS-19 | 0.25 | 1.00 | 4.00 |
| K. oxytoca 1082E | >128 | >128 | >128 |
| S. marcescens | >128 | >128 | >128 |
| E. cloacae P 99 | >128 | >128 | >128 |
| P. aeruginosa 799/61 | >128 | >128 | >128 |
| P. aeroguinosa 3351 | >128 | >128 | >128 |
| P. aeroginosa BA | >128 | >128 | >128 |
| Helicobacter pylori K 1585 | 1 | | |
| Helicobacter pylori PH 81 | <0.1 | | |
| Staph. aureus 887 | ≦0.12 | 2.00 | 2.00 |
| Staph. aureus 25923 | ≦≦0.12 | 2.00 | 1.00 |
| Staph. haemolyticus 75 | ≦0.06 | 1.00 | >0.12 |
| E. faecalis 6 | ≦0.06 | 2.00 | ≦0.12 |
| B. subtilis ATCC 585369 | ≦0.12 | 2.00 | 2.00 |
| S. aureus 101 | >32 | 0.12 | |
| S. aureus 853 | 0.25 | | |
| S. haemolyticus 91 | 0.12 | | |

| Bacterial strain | Example 1<br>R¹ = R² = 2-F-phenol | Example 2<br>R¹ = R² = 2-CH₃-phenol | Example 3<br>R¹ = R² = 2-OCH₃-phenol | Example 4<br>R¹ = R² = 2-OCH₃-phenol (3-OH) | Example 8<br>R¹ = R² = –C₆H₄–OCH₃ | Example 9<br>R¹ = R² = –C₆H₄–OEt |
|---|---|---|---|---|---|---|
| E. coli 1346 | 32.00 | 2.00 | 64.00 | ≦0.25 | 8.00 | 16.00 |
| E. coli DC2 | >64 | 4.00 | 8.00 | 2.00 | 64.00 | >128 |
| E. coli 25922 | | 128 | >128 | >128 | >128 | >128 |
| E. coli 1527 E | >64 | | >128 | >128 | >12 | >128 |
| E. coli 159 R | 8.00 | >128 | | | | >128 |
| E. coli B | >64 | 0.50 | 16.00 | ≦0.25 | 8.00 | >128 |
| E. coli K12 KEA-12 (GyrA) | >64 | >128 | >128 | >128 | >128 | >128 |
| E. coli H560 | 8.00 | >128 | >128 | >128 | >128 | >128 |
| E. coli AS-19 | >64 | 4.00 | >128 | 1.00 | 32.00 | >128 |
| K. oxytoca 1082E | | >128 | >128 | >128 | >128 | >128 |
| S. marcescens | >64 | >128 | >128 | >128 | >128 | >128 |
| E. cloacae P 99 | >64 | >128 | >128 | >128 | >128 | >128 |
| P. aeruginosa 799/61 | >64 | >128 | >128 | >128 | >128 | >128 |
| P. aeroguinosa 3351 | >64 | >128 | >128 | >128 | >128 | >128 |
| P. aeroginosa BA | | >128 | >128 | >128 | >128 | >128 |
| Helicobacter pylori K 1585 | | 1 | | | | |
| Helicobacter pylori PH 81 | | <0.1 | | | | |
| Staph. aureus 887 | 16.00 | ≦0.25 | 8.00 | 0.50 | 0.50 | ≦0.5 |
| Staph. aureus 25923 | 8.00 | ≦0.25 | 4.00 | 0.50 | 1.000 | 2.00 |
| Staph. haemolyticus 75 | 0.25 | ≦0.25 | 4.00 | ≦0.25 | ≦0.25 | 1.00 |
| E. faecalis 6 | 2.00 | ≦0.25 | 4.00 | 32.00 | >128 | 64.00 |
| B. subtilis ATCC 585369 | | | 32.00 | ≦0.25 | 0.50 | ≦0.5 |
| S. aureus 101 | 8.00 | 0.50 | | ≦0.25 | | |
| S. aureus 853 | 16.00 | ≦0.25 | | | | |
| S. haemolyticus 91 | 8.00 | | | | | |

TABLE 1-continued

Antibacterial activity in vitro
Minimum inhibitory concentration (MIC) in µg/ml

| $R^1 = R^2$ 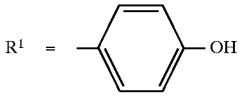 Example 10 | $R^1 =$ 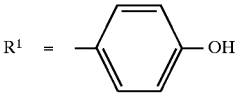 —OH $R^2 =$ 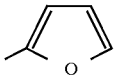 —OCH$_2$CH$_3$ Example 11 | $R^1 =$  —OH $R^2 =$ 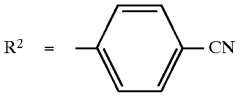 —CN Example 12 |
|---|---|---|
| 8.00 | 0.25 | 1.00 |
| 1.00 | 1.00 | 8.00 |
| >128 | >128 | >128 |
| >128 | | |
| | >128 | >128 |
| | 0.50 | 2.00 |
| >128 | >128 | >128 |
| >128 | >128 | >128 |
| 0.50 | 0.50 | 32.00 |
| >128 | >128 | >128 |
| >128 | | |
| >128 | >128 | >128 |
| >128 | >128 | >128 |
| >129 | >128 | >128 |
| >128 | >128 | >128 |
| | 1 | |
| | <0.1 | |
| 2.00 | 0.25 | 2.00 |
| 4.00 | 0.25 | 1.00 |
| 0.25 | 0.12 | 0.25 |
| >128 | 0.50 | 4.00 |
| | 0.25 | 2.00 |
| | 0.50 | 4.00 |
| | 0.25 | 2.00 |

The products in accordance with the invention can be used as medicaments, e.g. in the form of pharmaceutical preparations which contain them or their salts in admixture with a pharmaceutical, organic or inorganic carrier material which is suitable for parenteral or enteral administration, such as e.g. water, gelatine, gum arabic, lactose, starch, magnesium stearate, talc, vegetable oils, polyalkylene glycols, Vaseline, etc. The pharmaceutical preparations can be present in solid form, e.g. as tablets, dragées, suppositories, capsules, or in liquid form, e.g. as solutions, suspensions or emulsions. They may be sterilized and/or may contain adjuvants such as preservatives, stabilizers, wetting or emulsifying agents, salts for varying the osmotic pressure, anaesthetics or buffers. The compounds of formula I and their salts preferably come into consideration for parenteral administration and for this purpose are preferably formulated as lyophilizates or dry powders for dilution with usual agents such as water or isotonic saline.

The dosage of the compounds of general formula I and of the pharmaceutically compatible salts thereof with bases can vary within wide limits and in each individual case will, of course, be fitted to the individual requirements and to the pathogen to be controlled.

As mentioned earlier, medicaments containing a compound of general formula I or a pharmaceutically compatible salt thereof are likewise an object of the present invention, furthermore also a process for the production of such medicaments, which is characterized by bringing one or more compounds of general formula I or pharmaceutically compatible salts thereof and, if desired, one or more other therapeutically valuable substances into a galenical administration form.

The following Examples are intended to illustrate the present invention in more detail.

Synthesis of symmetrically-substituted bis-benzimidazoles

EXAMPLE 1

2-Fluoro-4-[2'-(3-fluoro-4-hydroxy-phenyl)-6,6'-dibenzimidazol-2-yl]-phenol

Method A 0.43 g (2 mmol) of 3,3;-diamino-benzidine and 0.56 g (4 mml) of 3-fluoro-4-hydroxy-benzaldehyde were dissolved in 50 ml of ethanol and treated with a solution of 0.38 g (2 mmol) of Na$_2$S$_2$O$_5$ and 5 ml of water. The reaction solution was stirred under reflux for 16 hours. Insoluble products were filtered off. The product was precipitated by adding 60 ml of water and was then filtered off and treated with 100 ml of hot methanol. The methanolic solution was filtered and the filtrate was treated with a methanolic HCl solution. After partial distillation of the solvent the dihydrochloride salt separated in the form of beige crystals. Yield: 610 mg (58%).

EXAMPLE 2

2,2'-Dimethyl-6,6'-dibenzimidazol-2,2'-ylene-diphenol 2.14 g (10 mmol) of 3,3'-diaminobenzidine, 2.72 g (20 mmol) of 4-hydroxy-3-methylbenzaldehyde and 1.9 g (10 mmol) of Na$_2$S$_2$O$_5$ gave 1.1 g of dihydrochloride in the form of colourless crystals analogously to method A. Yield: 47%.

EXAMPLE 3

4-[2'-(4-Hydroxy-3-methoxy-phenyl)-6,6'-dibenzimidazol-2-yl]-2-methoxy-phenyl 1.07g (5 mmol) of 3,3'-diamino-benzidine, 1.54 g (10 mmol) of 4-hydroxy-3-methoxybenzaldehyde and 0.95 g (5 mmol) of $Na_2S_2O_5$ gave 0.2 g of dohydrochloride in the form of beige crystals analogously to method A. Yield: 8%.

EXAMPLE 4

5-[2'-(3-Hydroxy-4-methoxy-phenyl)-6,6'-dibenzimidazol-2-yl]-2-methoxy-phenol 1.07 g (5 mmol) of 3,3'-diamino-benzidine, 1.54 g (10 mmol) of 3-hydroxy-4-methoxybenzaldehyde and 0.95 g (5 mmol) of $Na_2S_2O_5$ gave 0.4 g of dihydrochloride in form of beige crystals analogously to method A. Yield: 17%.

EXAMPLE 5

4-[2'-(4-Hydroxy-phenyl)-6,6'-dibenzimidazol-2-yl)-phenol hydrochloride 4.29 g (20 mmol) of 3,3'-diamino-benzidine, 4.88 g (40 mmol) of 4-hydroxybenzaldehyde and 3.8 g (20 mmol) of $Na_2S_2O_5$ gave 2.09 g of dihydrochloride in form of beige crystals analogously to method A. Yield: 25%.
Method B
2.14 g (10 mmol) of 3,3'-diamino-benzidine and 4.05 g (20 mmol) of 4-hydroxy-benzoic acid ethyl imido ester hydrochloride were dissolved in 300 ml of ethanol and boiled at reflux for 2 hours. The reaction solution was subsequently cooled to room temperature. After the addition of 200 ml of water, a fine white precipitate separated. The precipitate was filtered off and recrystallized from a methanolic HCl solution. The dihydrochloride salt was obtained in the form of beige crystals. Yield: 1.45 g (25%).

EXAMPLE 6

3-[2'-(3-Hydroxy-phenyl)-6,6'-dibenzimidazol-2-yl]-phenol 1.07 g (5 mmol) of 3,3'-diamino-benzidine, 1.22 g (10 mmol) of 3-hydroxy-benzaldehyde and 0.95 g (5 mmol) of $Na_2S_2O_5$ gave 1.2 g of dihydrochloride in the form of beige crystals analogously to method A. Yield: 57%.

EXAMPLE 7

4-[2'-(4-Amino-phenyl)-6,6'-dibenzimidazol-2-yl]-phenylamine 5.35 g (25 mmol) of 3,3'-diamino-benzidine, 5.55 g (50 mmol) of 4-amino-benzaldehyde and 4.75 g (25 mmol) of $Na_2S_2O_5$ gave 0.35 g of dihydrochloride in the form of beige crystals analogously to method A. Yield: 5%.

EXAMPLE 8

2,2'-Bis-(4-methoxy-phenyl)-6,6'-dibenzimidazole 1.07 g (5 mmol) of 3,3'-diamino-benzidine, 1.36 g (10 mmol) of 4-methoxy-benzaldehyde and 0.95 g (5 mmol) of $Na_2S_2O_5$ gave 0.41 g of dihydrochloride in the form of colourless crystals analogously to method A. Yield: 18%.
Method C
A mixture of 1.07 g (5 mmol) of 3,3'-diamino-benzidine and 1.49 g (11 mmol) of 4-methoxy-benzaldehyde dissolved in 50 ml of nitrobenzene was stirred at 140° C. for 24 hours. After cooling to room temperature the reaction solution was concentrated by vacuum distillation. The residue obtained was purified chromatographically over a Florosil column. The eluting agent used was $CH_2Cl_2/CH_3OH$ (98:2–90:10). The corresponding fraction was collected and gave 1.34 g of 2,2'-bis-(4-methoxy-phenyl)-6,6'-dibenzimidazole in the form of a beige solid. Yield: 56%.

EXAMPLE 9

2,2'-Bis-(4-ethoxy-phenyl)-6,6'-dibenzimidazole 2.14 g (10 mmol) of 3,3'-diamino-benzidine, 3.0 g (20 mmol) of 4-ethoxybenzaldehyde and 1.9 g (10 mmol) of $Na_2S_2O_5$ gave 3.4 g of dihydrochloride in the form of white crystals analogously to method A. Yield: 72%.

EXAMPLE 10

2,2'-Difuran-2-yl-6,6'-dibenzimidazole 0.64 g (3 mmol) of 3,3'-diamino-benzidine and 1.05 g (6 mmol) of furan-2-carboxylic acid ethyl imido ester gave 0.16 g of dihydrochloride in the form of beige crystals analogously to method B. Yield 12%.

Synthesis of asymmetrically-substituted bis-benzimidazoles

EXAMPLE 11

4-[2'-(4-Ethoxy-phenyl)-6,6'-dibenzimidazol-2-yl]-phenol 3.15 g (15 mmol) of 3,3'-diamino-benzidine, 1.83 g (15 mmol) of 4-hydroxybenzaldehyde and 2.75 g (15 mmol) of 4-ethoxybenzaldehyde were dissolved in 100 ml of ethanol and treated with 2.85 g (15 mmol) of $Na_2S_2O_5$ dissolved in 20 ml of water. The reaction mixture was boiled at reflux for 24 hours and subsequently filtered. 100 ml of water were added to the filtrate in order to precipitate the product. The solid was filtered off and purified by column chromatography (400 g of silica gel; methylene chloride:methanol (9:1) was used as the eluent). The product was recrystallized from methanol. 0.4 g of yellowish crystals formed. Yield: 6%.

EXAMPLE 12

4-[2'-(4-Hydroxy-phenyl)-6,6'-dibenzimidazol-2-yl]-benzonitrile 4.28 g (20 mmol) of 3,3'-diamino-benzidine, 2.44 g (20 mmol) of 4-hydroxybenzaldehyde and 2.62 g (20 mmol) of 4 cyanobenzaldehyde were dissolved in 500 ml of ethanol and treated with 3.8 g (20 mmol) of $Na_2S_2O_5$ dissolved in 100 ml of water. The reaction mixture was boiled at reflux for 16 hours and subsequently filtered. The product was precipitated by adding 500 ml of water to the filtrate and the mixture was again filtered. The crude product (6.7 g) was purified by column chromatography (silica gel; methylene chloride:methanol (9:1) was used as the eluent). The product was recrystallized from methanol. 0.8 g of yellowish crystals of 4-[2'-(4-hydroxyphenyl)-6,6'-dibenzimidazol-2-yl]-benzonitrile was obtained. Yield: 10%.

Preparation of the intermediates

EXAMPLE 13

4-Hydroxy-benzoic acid ethyl imido ester 22.4 g (188 mmol) of 4-hydroxybenzonitrile were dissolved in 200 ml of chloroform and 50 ml ethanol. Dry HCl gas was introduced while stirring and cooling (the temperature of the solution should never exceed 20° C.) until the solution was saturated. The hydrochloride separated as a white crystalline precipitate. After 2 hours the reaction solution was filtered and the crude product was suspended in 150 ml of ethanol. Dry HCl gas was again conducted into the solution while stirring and cooling (the temperature of the solution should be about 20° C.) until it was saturated. The white crystals were filtered off and used without further purification. Yield: 18.0 g. M.p.: 207°–209° C. (dec.).

EXAMPLE 14

Furan-2-carboxylic acid ethyl imido ester

The synthesis was effected in analogy to Example 13.

9.3 g (0.2 mol) of 2-cyano-furan gave 4.8 g of colourless crystals. Yield: 27% of the corresponding imido ester hydrochloride. M.p.: 117°–119° C.

TABLE 2

Characteristics of the compounds of Examples 1–12

| Example No. free base; hydrochloride | $^1$H-nmr spectra* | Rf Values** | M.p. (°C.) |
|---|---|---|---|
| 4 | 6.94 (d, 4H); 7.52 (dd, 2H); 7.63 (dd, 2H); 7.78 (s, 2H), 8.04 (d, 4H). | 0.09 (9:1) | >260 |
| 4 (2HCl) | 7.11 (d, 4H); 7.89 (s, 4H); 8.01 (s, 2H); 8.26 (d, 4H) | 0.77 (3:1) | |
| 5 | 6.92 (dd, 2H); 7.37 (t, 2H); 7.55–7.70 (m, 8H); 7.84 (s, 2H) | 0.29 (9:1) | >260 |
| 5 (2HCl) | 7.19 (dd, 2H); 7.53 (t, 2H); 7.73 (s, 2H); 7.82 (d, 2H); 7.94 (m, 4H); 8.07 (s, 2H) | | |
| 6 | 6.74 (d, 4H); 7.68 (m, 4H); 7.86 (s, 2H); 7.91 (d, 4H) | 0.09 (9:1) | >260 |
| 6 (2HCl) | 6.80 (d, 4H); 7.84 (s, 4H); 7.95 (s, 2H); 8.09 (d, 4H) | 0.63 (3:1) | |
| 1 | 7.12 (t, 2H); 7.54 (d, 2H); 7.65 (d, 2H); 7.81 (s, 2H); 7.88 (dd, 2H); 7.96 (dd, 2H) | 0.15 (9:1) | >260 |
| 2 (2HCl) | 7.29 (t, 2H); 7.88 (s, 4H); 8.00 (s, 2H); 8.09 (dd, 2H); 8.27 (dd, 2H) | | |
| 2 | 2.24 (s, 6H); 6.94 (d., 2H); 7.50 (dd, 2H); 7.61 (dd, 2H), 7.77 (s, 2H); 7.86 (dd, 2H); 7.95 (s, 2H) | 0.0 (0:1) | >260 |
| 2 (2HCl) | 2.25 (s, 6H); 7.12 (d, 2H); 7.86 (s, 4H); 7.97 (s, 2H); 8.11 (dd, 2H); 8.16 (d, 2H) | 0.80 (3:1) | |
| 3 | 3.91 (s, 6H); 6.94 (d, 2H); 7.52 (dd, 2H); 7.6–7.7 (m, 4H); 7.78 (d, 4H) | 0.2 (9:1) | >260 |
| 3 (2HCl) | 3.96 (s, GH); 7.10 (d, 1H); 7.85–7.92 (m, 6H); 8.01 (s, 2H); 8.09 (d, 2H) | | |
| 7 | 3.87 (s, 6H); 7.11 (d, 2H); 7.50–7.70 (m, 10H) | 0.20 (9:1) | >260 |
| 7 (2HCl) | 3.93 (s, 6H); 7.28 (d, 2H); 7.72 (s, 2H); 7.82 (d, 2H); 7.86 (s, 4H); 7.99 (s, 2H) | | |
| 8 | 3.86 (s, 6H); 7.13 (d, 4H); 7.53 (d, 2H); 7.66 (d, 2H); 7.82 (s, 2H); 8.16 (d, 4H) | 0.59 (9:1) | >260 |
| 8 (2HCl) | 3.92 (s, 6H); 7.30 (d, 4H); 7.88 (q, 4H); 8.00 (s, 2H); 8.37 (d, 4H) | | |
| 9 | 1.38 (t, 6H); 4.13 (q, 4H); 7.12 (d, 4H); 7.55 (dd, 2H); 7.66 (d, 2H); 7.82 (s, 2H); 8.14 (d, 4H) | 0.41 (9:1) | >260 |
| 9 (2HCl) | 1.39 (t, 6H); 4.18 (q, 4H); 7.25 (d, 4H); 7.84 (q, 4H); 7.97 (s, 2H); 8.32 (d, 4H) | | |
| 10 | 6.80 (d, 2H); 7.37 (d, 2H); 7.62 (d, 2H); 7.70 (d, 2H); 7.85 (s, 2H); 8.04 (s, 2H) | 0.45 (9:1) | >260 |
| 10 (2HCl) | 6.95 (dd, 2H); 7.79 (d, 2H); 7.85 (s, 4H); 7.98 (s, 2H); 8.26 (dd, 2H) | | |
| 11 | 1.38 (t, 3H); 4.17 (q, 2H); 7.06 (d, 2H); 7.20 (d, 2H); 7.70–7.70 (m, 4H); 7.94 (s, 2H); 8.18 (d, 2H); 8.25 (d, 2H) | 0.25 (9:1) | >260 |
| 11 (2HCl) | 1.39 (t, 3H); 4.19 (q, 2H); 7.11 (d, 2H); 7.27 (d, 2H); 7.88 (s, 4H); 8.00 (s, 2H); 8.26 (d, 2H); 8.35 (d, 2H) | | |
| 12 | 6.94 (d, 2H); 7.54 (dd, 1H); 7.62 (t, 2H); 7.75 (brosf s, 1H); 7.82 (s, 2H); 8.04 (d, 2H); 8.06 (d, 2H); 8.38 (d, 2H) | 0.22 (9:1) | >260 |
| 12 (2HCl) | 7.12 (d, 2H); 7.74 (d, 1H); 7.85 (d, 1H); 7.90 (s, 2H); 8.01 (s, 2H); 8.12 (d, 2H); 8.24 (d, 2H); 8.45 | (d, 2H) | |

*$^1$H-nmr spectra were taken at 250 MHz in DMSO-d$_6$ at a temperature of 298° K. The concentration of the compounds Iay at 2 mmol. The chemical shifts δ (± 0.02 ppm) were measured relative to δ (TMS) = 0.0 ppm; s = singlet, d = doublet, t = triplet, q = quartet, m = multiplet.
**The Rf values were measured on a Si-coated glass plate (Merck). The eluent used was a mixture of 9 parts by volume of methylene chloride and 1 part of methanol (9:1) or a solution of 3 parts by volume of methylene chloride and 1 part of methanol (3:1).

Example A

Ampoules for an intramuscular administration are produced in the usual manner:

A lyophilizate of 1 g of 4-[2'-(4-hydroxy-phenyl)-6,6'-dibenzimidazol-2-yl]-phenol hydrochloride (1:2) is produced in the usual manner and filled into an ampoule. Prior to administration the lyophilizate is treated with 2.5 ml of 2% lidocaine hydrochloride solution.

Example B

Tablets of the following composition are produced in the usual manner:

|  | mg/tablet |
| --- | --- |
| 4-[2'-(4-Amino-phenyl)-6,6'-dibenzimidazol-2-yl]-phenylamine | 1 |
| Lactose | 103 |
| Corn starch | 25 |
| Microcrystalline cellulose | 70 |
| Magnesium stearate | 1 |
| Total | 200 |

Example C

Capsules of the following composition are produced:

|  | mg/capsule |
| --- | --- |
| 2,2'-Dimethyl-6,6'-dibenzimidazol-2,2'-ylene-diphenol | 1 |
| Lactose | 164 |
| Corn starch | 30 |
| Talc | 5 |
| Total | 200 |

The active substance, lactose and maize starch are firstly mixed in a mixer and then in a comminuting machine. The mixture is returned to the mixer, the talc is added and the mixture is mixed thoroughly. The mixture is filled by machine into hard gelatine capsules.

We claim:

1. Compounds useful as antibacterial agents selected from the group consisting of:
   2-fluoro-4-[2'-(3-fluoro-4-hydroxyphenyl)-6,6'-dibenzimidazol-2-yl]-phenol,
   4-[2'-(4-hydroxy-3-methoxy-phenyl)-6,6'-dibenzimidazol-2-yl]-2-methoxy-phenol,
   5-[2'-(3-hydroxy-4-methoxy-phenyl)-6,6'-dibenzimidazol-2-yl]-2-methoxy-phenol,
   2,2'-bis-(4-methoxy-phenyl)-6,6'-dibenzimidazole,
   2,2'-bis-(4-ethoxy-phenyl)-6,6'-dibenzimidazole,
   4-[2'-(4-ethoxy-phenyl)-6,6'-dibenzimidazol-2-yl]-phenol,
   4-[2'-(4-hydroxy-phenyl)-6,6'-dibenzimidazol-2-yl]-benzonitrile,
   2,2'-difuran-2-yl-6,6'-dibenzimidazole,
   as well as the pharmaceutically acceptable salts thereof.

2. The compound according to claim 1, 2-fluoro-4-[2'-(3-fluoro-4-hydroxy-phenyl)-6,6'-dibenzimidazol-2-yl]-phenol.

3. The compound according to claim 1, 4-[2'-(4-hydroxy-3-methoxy-phenyl)-6,6'-dibenzimidazol-2-yl]-2-methoxy-phenol.

4. The compound according to claim 1, 5-[2'(3-hydroxy-4-methoxy-phenyl)-6,6'-dibenzimidazol-2-yl]-2-methoxy-phenol.

5. The compound according to claim 1, 2,2'-bis-(4-methoxy-phenyl)-6,6'-dibenzimidazole.

6. The compound according to claim 1, 2,2'-bis-(4-ethoxy-phenyl)-6,6'-dibenzimidazole.

7. The compound according to claim 1, 4-[2'(4-ethoxy-phenyl)-6,6'-dibenzimidazol-2-yl]-phenol.

8. The compound according to claim 1, 4-[2'-(4-hydroxy-phenyl)-6,6'-dibenzimidazol-2-yl]-benzonitrile.

9. The compound according to claim 1, 2,2'-difuran-2-yl-6,6'-dibenimidazole.

10. A pharmaceutical composition useful against bacterial pathogens comprising a compound of claim 1 as well as the pharmaceutically acceptable salts thereof, and one or more therapeutically inert excipients.

11. A method of treating bacterial illness comprising administering a compound having the formula

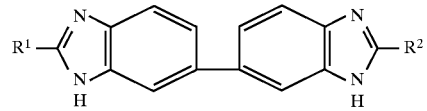

wherein $R^1$ and $R^2$ may be the same or different and signify $C_6H_4R^3-$, $C_6H_3(OH)R^4-$ or heterocyclyl, $R^3$ signifies hydroxy, amino, lower alkoxy or cyano, and $R^4$ signifies halogen, lower alkyl or lower alkoxy, as well as the pharmaceutically acceptable salts thereof, and one or more therapeutically inert excipients.

12. The method of treating bacterial illnesses of claim 11 wherein $R^3$ and $R^4$ occupy a 4-position when mono substituted on the phenyl ring or a 3- and 4- position when disubstituted on the phenyl ring.

* * * * *